(12) United States Patent
Maris et al.

(10) Patent No.: US 11,122,755 B2
(45) Date of Patent: Sep. 21, 2021

(54) WHITE RUST RESISTANT CHRYSANTHEMUM PLANTS

(71) Applicant: Dümmen Group B.V., De Lier (NL)

(72) Inventors: Paulus Cornelis Maris, De Lier (NL); Johannes Franciscus Johanna Maria van den Heuvel, Rotterdam (NL)

(73) Assignee: Dümmen Group B.V.

( * ) Notice: Subject to any disclaimer, the term of this patent is extended or adjusted under 35 U.S.C. 154(b) by 160 days.

(21) Appl. No.: 16/335,388

(22) PCT Filed: Aug. 29, 2017

(86) PCT No.: PCT/EP2017/071647
§ 371 (c)(1),
(2) Date: Mar. 21, 2019

(87) PCT Pub. No.: WO2018/065151
PCT Pub. Date: Apr. 12, 2018

(65) Prior Publication Data
US 2019/0218570 A1 Jul. 18, 2019

(30) Foreign Application Priority Data
Oct. 4, 2016 (WO) .................. PCT/EP2016/073672

(51) Int. Cl.
*A01H 6/14* (2018.01)
*A01H 1/00* (2006.01)
*A01H 5/02* (2018.01)
*C12N 15/82* (2006.01)

(52) U.S. Cl.
CPC .............. *A01H 1/1255* (2021.01); *A01H 1/00* (2013.01); *A01H 5/02* (2013.01); *A01H 6/1424* (2018.05); *C12N 15/8282* (2013.01)

(58) Field of Classification Search
CPC ............................ A01H 6/1424; A01H 1/1255
See application file for complete search history.

(56) References Cited

U.S. PATENT DOCUMENTS

| PP14,916 P2 | 6/2004 | Post |
| 10,743,497 B2 * | 8/2020 | Maris .................. A01H 6/1424 |
| 2018/0352773 A1 | 12/2018 | Maris et al. |

FOREIGN PATENT DOCUMENTS

| KR | 1020160099179 A | 8/2016 |
| WO | 2017060238 A1 | 4/2017 |

OTHER PUBLICATIONS

Martin et al Plant Pathology vol. 19, pp. 180-184 (Year: 1970).*
De Backer, "Characterization and detection of Puccinia horiana on chrysanthemum for resistance breeding and sustainable control", 2012, 217 pages, Ghent University Faculty of Bioscience Engineering, Ghent, Belgium.
Martin et al., "Resistance of Chrysanthemum Cultivars to White Rust (*Puccinia horiana*)", Plant Pathology, 1970, pp. 180-184, vol. 19, No. 4.

* cited by examiner

*Primary Examiner* — David H Kruse
(74) *Attorney, Agent, or Firm* — The Webb Law Firm (57) ABSTRACT

The present invention relates to white rust resistant plants of the genus *Chrysanthemum* and to seeds, plant parts, plant cells and progeny thereof. The present invention further relates to means, and particularly molecular markers for identifying white rust resistant plants of the genus *Chrysanthemum*. Specifically, the present invention relates to plants belonging to the genus *Chrysanthemum*, the plants are resistant to white rust and the plants comprise in their genome at least one genomic region, or gene or allele, providing white rust resistance, the at least one genomic region, or gene or allele, providing white rust resistance is genetically linked to a nucleic acid sequence comprised in at least one copy in the genome of the resistant plants and is represented by SEQ ID No. 3.

20 Claims, 4 Drawing Sheets
Specification includes a Sequence Listing.

WHITE RUST RESISTANT CHRYSANTHEMUM PLANTS

CROSS-REFERENCE TO RELATED APPLICATIONS

This application is the United States national phase of International Application No. PCT/EP2017/071647 filed Aug. 29, 2017, and claims priority to International Application No. PCT/EP2016/073672 filed Oct. 4, 2016, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1901712_ST25.txt. The size of the text file is 3,236 bytes, and the text file was created on Mar. 15, 2019.

The present invention relates to white rust resistant plants of the genus *Chrysanthemum* and to seeds, plant parts, plant cells and progeny thereof. The present invention further relates to means, and particularly molecular markers, for identifying white rust resistant plants of the genus *Chrysanthemum*.

Chrysanthemums, also designated as chrysant(h)s, are flowering plants of the genus *Chrysanthemum* in the family Asteraceae. The plants are native to Asia and north-eastern Europe and are comprised of a large number of horticultural varieties and cultivars.

Several genera of Chrysanthemums amongst which the economically important florist's Chrysanthemums were classified in the genus *Dendranthema* in the past. However, presently, the florist's Chrysanthemums are reclassified as *Chrysanthemum indicum*, restoring the position of these Chrysanthemums in the genus *Chrysanthemum*.

Naturally occurring *Chrysanthemum* species are herbaceous perennial plants. These *Chrysanthemum* species display alternately arranged leaves divided into leaflets with toothed or occasionally smooth edges. Chrysanthemums were first cultivated in China as a flowering herb as far back as the 15th century BC and over 500 cultivars had been recorded by the year 1630.

Presently cultivated Chrysanthemums display a more pronounced and aesthetic flowering as compared to their wild relatives. The flower heads occur in various forms, and can be daisy-like or decorative, like pompons or buttons. This genus contains many hybrids and thousands of cultivars developed for horticultural purposes. In addition to the traditional yellow, other colours are available, such as white, purple, and red. The most important hybrid is *Chrysanthemum* x *morifolium*, also designated as *Chrysanthemum* x *grandiflorum*, being primarily derived from *Chrysanthemum indicum*.

Chrysanthemums can be divided into two basic groups, garden hardy and exhibition. Garden Chrysanthemums are perennials capable of wintering in most northern latitudes. Exhibition varieties are generally not capable of surviving winter. Garden Chrysanthemums can be defined by their ability to produce an abundance of small blooms with little if any mechanical assistance, such as staking, and being able to withstand wind and rain. Exhibition varieties generally require staking, overwintering in a relatively dry, cool environment, and sometimes the addition of night lights.

White rust is a disease in plants caused by Basisiomycota. Basisiomycota form a distinct phylogenetic lineage of fungus-like eukaryotic microorganisms. They are filamentous, microscopic, absorptive organisms that reproduce both sexually and asexually. Basiodiomycetes occupy both saprophytic and pathogenic lifestyles, and include some of the most notorious pathogens of plants, causing devastating diseases such as southern blight of potato, tomato and a wide range of ornamentals and stem rust of wheat. The basidiomycetes are best known for the production of large fruit bodies such as mushrooms, puffballs and brackets and are important organisms in the decay of wood and leaf litter.

In *Chrysanthemum*, white rust is a disease generally caused by the pathogenic basidiomycete or fungus *Puccinia horiana*. *Chrysanthemum* specific symptoms include white rust spots on the upper surfaces of leaves. These spots are initially pale-green to yellow in colour and up to 5 mm in diameter, but may turn brown as the tissue becomes necrotic. On the underside of the leaf, the spots develop into pink or white pustules that become prominent as the teliospores develop. The disease is generally carried on infected cuttings and plants, including cut flowers, of glasshouse Chrysanthemums.

Until 1963, *Puccinia horiana* was confined to China and Japan. However, it has since spread rapidly on infected imported cuttings and is now a feared and serious disease in nurseries in Europe. A large number of pathotypes of *P. horiana* is known, and great differences of virulence of pathotypes of *P. horiana* after inoculation on various *Chrysanthemum* cultivars was demonstrated (De Backer, 2012). The *P. horiana* pathotype NL1, collected in 2006 in The Netherlands showed to be the most virulent one.

Preventive spraying with fungicides is effective but costly. When the climate is very suitable for white rust even preventive sprays are not effective enough and susceptible varieties are highly likely to be infected. Active ingredients found useful include oxycarboxin, triforine, benodanil, triadimefon, diclobutrazol, bitertanol and propiconazole. *Verticillium lecanii* has been suggested for biological control of on glasshouse Chrysanthemums.

Considering the considerable damage to *Chrysanthemum* cultivation by white rust, there is a need in the art to provide new genetic resistant sources, i.e. there is a need in the art for new resistance genes providing durable white rust resistance to plants of the genus *Chrysanthemum*.

It is an object of the present invention, amongst other objects, to meet the above need of the art.

According to the present invention, this object is met by the present invention by providing plants, plant parts, seeds and means as outlined in the appended claims.

Specifically, according to a first aspect, this object of the present invention, amongst other objects, is met by providing plants belonging to the genus *Chrysanthemum*, the plants are resistant to white rust and the plants comprise in their genome at least one genomic region, or gene or allele, providing white rust resistance, the at least one genomic region, or gene, providing white rust resistance is genetically linked to a nucleic acid sequence comprised with at least one copy in the genome of said resistant plant and is represented by SEQ ID No. 3. Considering the hexaploid nature of plants belonging to the genus *Chrysanthemum*, SEQ ID No. 3 is preferably present in the genome of the resistant plants with at least one copy, such as 2, 3, 4, 5 or 6 copies per resistant plant.

Within the context of the present invention, the terms "genomic region" or "genomic regions" indicate distinct nuclear sequences encoding one or more white rust resistance providing genes such as one gene.

The sequence SEQ ID No. 3 is genetically linked to white rust resistance providing genomic regions or genes, or formulated differently, SEQ ID No. 3 is a molecular marker indicative for the presence of white rust resistance providing genomic regions or genes. SEQ ID No. 3, and other sequences presented herein, can be obtained by submitting a sample comprising genomic DNA of a white rust resistant plant of the genus *Chrysanthemum*, such as the deposits identified herein, to a restriction digestion with the restriction enzymes Mse1 and EcoR1 optionally in combination a nucleic acid amplification using primers pairs developed based on the sequences provided herein.

Although detecting the presence of SEQ ID No. 3 is sufficient to establish whether a plant of the genus *Chrysanthemum* is resistant to white rust, the resistance can additionally be confirmed by a disease assay such as the disease assay outlined below.

A disease assay can be conducted on cuttings or small plants inside closed plastic containers 125 cm length×80 cm width×35 cm height using a plastic cover. White rust infected inoculum plants are placed in the containers (36 inoculum plants per container evenly distributed among 265 cuttings). An isolate derived from *P. horiana* pathotype NL1 can be used (the original NL1 pathotype was obtained from the Plantenziektenkundige Dienst, Wageningen, NL).

Because white rust requires a high relative humidity and a water film on the leaves, the small plants or cuttings, the inner sides of the plastic container and the cover are preferably fogged with demineralized water in combination with a wet cloth at the bottom of the plastic container. After preparing the experimental setup, the aquaria are placed in a growth chamber at 18° C. covered with white plastic to create a dark, humid environment for four days. Every day the containers are ventilated to ensure a good dispersal of the spores through the whole container. After removing the white plastic the containers are illuminated with a combination of mercury and SON-T lights during 18 hours per day (6000 Lux).

Generally, disease symptoms can be assessed 21 to 28 days post infection. Plants are scored according to a scale of 1 (infection) to 9 (not infected) wherein a scores of 1-3 indicate the plant as being susceptible, 4-6 indicates the plant as being intermediate resistant and 7-9 indicates the plant as being resistant.

Preferably, the present plants further comprise in their genome a further genomic region, or gene, providing white rust resistance, the further white rust resistance providing genomic region, or gene, is genetically linked to a nucleic acid sequence comprised with at least one copy in the genome of the resistant plants and is represented by SEQ ID No. 2 or SEQ ID No. 1. Considering the hexaploid nature of plants belonging to the genus *Chrysanthemum*, SEQ ID No. 2 and SEQ ID No. 1 are preferably present, independently of each other, in the genome of the resistant plants with at least one copy, such as 2, 3, 4, 5 or 6 copies per resistant plant.

According to an especially preferred embodiment, the present plants further comprise in their genome a further genomic regions, or genes, providing white rust resistance, the further white rust resistance providing genomic regions, or genes, are genetically linked to nucleic acid sequences comprised with at least one copy in the genome of said resistant plant and are represented by SEQ ID No. 1 and SEQ ID No. 2, respectively. Considering the hexaploid nature of plants belonging to the genus *Chrysanthemum*, SEQ ID No. 2 and SEQ ID No. 1 are preferably present, independently of each other, in the genome of the resistant plants with at least one copy, such as 2, 3, 4, 5 or 6 copies per resistant plant.

The present inventors identified further genomic sequences which are although being similar (but not identical) to SEQ ID No. 3, and present in the white rust resistance genomic region, locus or gene not responsible for conferring resistance to white rust. As such the genomic sequences similar (but not identical) to SEQ ID No. 3 are referred to as susceptibility alleles or susceptibility genomic sequences. Accordingly, according a preferred embodiment, the present plants comprises five copies or less per plant of these similar (but not identical) nucleic acid sequences comprised in the genome of the resistant plants selected from the group consisting of SEQ ID No. 4, SEQ ID No. 5, SEQ ID No. 6, SEQ ID No. 7, SEQ ID No. 8 and SEQ ID No. 9. Considering the hexaploid nature of plants belonging to the genus *Chrysanthemum*, SEQ ID Nos 4 to 9 are preferably present, independently of each other, in the genome of the resistant plants with 4 copies or less such as 3, 2, 1 or 0 copies. In the latter case, the plants of the present invention comprise 6 copies of SEQ ID No. 3.

The present plants are preferably a cut *Chrysanthemum* plant or a pot *Chrysanthemum* plant. Cut *Chrysanthemum* plants and pot *Chrysanthemum* plants are also designated in the art as cut flowers and potted plants, respectively. Sometimes, also reference is made to garden Chrysanthemums being a garden proof version of a pot *Chrysanthemum* plant.

According to a preferred embodiment of the invention, the present plants belonging to the genus *Chrysanthemum* are selected from the group consisting of *Chrysanthemum* x *morifolium; Chrysanthemum* x *grandiflorum; Chrysanthemum* x *rubellum; Chrysanthemum abolinii; Chrysanthemum achillaea L.; Chrysanthemum alabasicum; Chrysanthemum brachyanthum; Chrysanthemum carinatum; Chrysanthemum chalchingolicum; Chrysanthemum cinerariifolium; Chrysanthemum coccineum; Chrysanthemum coreanum; Chrysanthemum coronarium; Chrysanthemum decaisneanum; Chrysanthemum delavayanum; Chrysanthemum dichrum; Chrysanthemum fastigiatum; Chrysanthemum frutescens; Chrysanthemum gracile; Chrysanthemum grubovii; Chrysanthemum horaimontanum; Chrysanthemum hypoleucum; Chrysanthemum indicum L.; Chrysanthemum junnanicum; Chrysanthemum kinokuniense; Chrysanthemum kokanicum; Chrysanthemum konoanum; Crysanthemum majus; Chrysanthemum marginatum; Chrysanthemum mawei; Chrysanthemum maximum L.; Chrysanthemum miyatojimense; Chrysanthemum morifolium; Chrysanthemum multifidum; Chrysanthemum nitidum; Chrysanthemum parvifolium; Chrysanthemum przewalskii; Chrysanthemum purpureiflorum; Chrysanthemum ramosum; Chrysanthemum rhombifolium; Chrysanthemum roborowskii; Chrysanthemum segetum; Chrysanthemum shihchuanum; Chrysanthemum shimotomaii; Chrysanthemum trilobatum; Chrysanthemum tripinnatisectum; Chrysanthemum vestitum; Chrysanthemum vulgare* (*L.*); *Chrysanthemum yoshinyanthemum; and Chrysanthemum zawadskii.*

According to another preferred embodiment of the present invention, the causative pathogen causing the present white rust disease is *Puccinia horiana. Puccinia horiana* is an autoecious rust. The bicellular teliospores germinate in situ to produce unicellular basidiospores which are dispersed in air currents. No other spores are known. High humidity, and a film of moisture, appear to be necessary for the germination of both teliospores and basidiospores. Teliospores are capable of germination as soon as they are mature; germination and discharge of basidiospores occur between 4° C. and 23° C. and, at an optimum temperature of 17° C., discharge of basidiospores is observed within 3 hours. Basidiospores can germinate over a wide temperature range and, at 17-24° C., either surface of the leaf may be penetrated within 2 hours. Thus, only 5 hours of wetness is sufficient for a new infection to become established. Within the leaf, abundant, hyaline, intercellular hyphae are produced with intracellular haustoria. The incubation period is normally 7-10 days, but short periods of high temperatures (over 30° C.) can prolong the period to 8 weeks.

Following infection, pale-green to yellow spots, up to 5 mm in diameter, develop on the upper surface of leaves. The centres of these spots become brown and necrotic with aging. On the corresponding lower surface, raised, buff or pinkish, waxy pustules (telia) are found. As the spots on the upper surface become sunken, these pustules become quite prominent and turn whitish when basidiospores are produced. Telia are occasionally found on the upper leaf surface. Severely attacked leaves wilt, hang down the stem and gradually dry up completely.

According to yet another preferred embodiment, the present invention relates to plants comprising at least one genomic region, or gene, providing white rust resistance derived from a *Chrysanthemum* plant deposited under number NCIMB 42762 on May 31, 2017. A *Chrysanthemum* plant deposited under number NCIMB 42762 can be obtained through the National Collection of Industrial, Food and Marine Bacteria (NCIMB), NCIMB Ltd., Ferguson Building, Craibstone Estate, Bucksburn, Aberdeen AB21 9YA, United Kingdom.

According to still another preferred embodiment, the present plants further comprise at least one genomic region, or gene or allele, providing white rust resistance derived from a *Chrysanthemum* plant deposited under number NCIMB 42455 on Mar. 14, 2016 or the present plants further comprise at least two genomic regions, or genes or alleles, providing white rust resistance derived from a *Chrysanthemum* plant deposited under number NCIMB 42455. Formulated differently, the present plants preferably stack resistance genes against white rust, i.e. comprise one genomic region, or gene or allele, genetically linked to SEQ ID No. 3 derived from deposit NCIMB 42762 and one or two genomic regions, or genes, derived from NCIMB 42455 genetically linked to SEQ Nos. 1 or 2, respectively.

According to a most preferred embodiment, the present invention relates to a *Chrysanthemum* x *morifolium* plant being resistant to the white rust pathogen *Puccinia horiana*.

Considering the importance of white rust resistant genetic sources in the art, such as the present plants, the present invention, according to a second aspect, relates to seeds, plant parts or plant cells of the present plants. The present seeds, plant parts or plant cells comprise in their genome SEQ ID No 0.3, and preferably further SEQ ID No. 2 or SEQ ID No. 1, most preferably SEQ ID No. 2 and SEQ ID No. 1 and are, accordingly, capable of providing, or cultivated into, plants being resistant to white rust and especially white rust caused by an infection with *Puccinia horiana*.

According to a third aspect, the present invention also relates to progeny of the present *Chrysanthemum* plants. Progeny of the present plants can be readily identified by establishing the presence of SEQ ID No. 3, and preferably further SEQ ID No. 2 or SEQ ID No. 1, most preferably SEQ ID No. 2 and SEQ ID No. 1 in their genome.

According to a fourth aspect, the present invention relates to the use of SEQ ID No. 3 for identifying a white rust resistant *Chrysanthemum* plant. Suitable methods, based on these SEQ ID Nos. for identifying such plant are generally known in the art such as methods based on nucleic acid amplification of genomic DNA and subsequent visualisation of amplification fragments although other techniques can be envisaged such as techniques based on hybridisation.

The present invention will be further detailed in the example presented below. In the examples, reference is made figure wherein.

EXAMPLES

Example 1

Introduction

Martin, P., & Firman, I. (1970). Resistance of *Chrysanthemum* Cultivars to White Rust (*Puccinia horiana*). *Plant Pathology*, 180-184 discloses several varieties of *Chrysanthemum* white rust resistant plants. In order to asses whether the genomic sequences linked white rust, i.e. SEQ ID Nos 1 and 2, are found in the disclosed *Chrysanthemum* cultivars, these cultivars were subjected to marker analyses and the results are presented in Table 1 below:

TABLE 1

Phenotype after inoculation with NL1 isolate of *P. horiana* of *Chrysanthemum* varieties previously reported by Martin (1970) to be resistant or immune to *P. horiana*.

| Variety | Phenotype according to Martin (1970) | Phenotype | SEQ ID No. 1[2] | SEQ ID No. 2 |
|---|---|---|---|---|
| Alec Bedser | Immune | N.t.[1] | – | – |
| Fred Shoesmith | Immune | Susceptible | – | – |
| Marlene | Immune | Susceptible | – | – |
| Polaris | Immune | Susceptible | – | – |
| Regalia | Immune | N.t. | + | – |
| Streamer | Immune | Susceptible | N.t. | N.t. |
| Sweetheart | Immune | Susceptible | – | – |
| Target | Immune | N.t. | – | – |
| Vibrant | Immune | N.t. | N.t. | N.t. |
| Bravo | Moderate resistant | Susceptible | N.t. | N.t. |
| Corsair | Practically immune | Susceptible | – | – |
| Discovery | Practically immune | Susceptible | – | – |
| Glamour | Practically immune | Resistant | + | – |
| Rivalry | Practically immune | Susceptible | – | – |

[1]N.t. = not tested
[2]–: SEQ ID is not present, +: gene is present

As can be clearly seen, none of the above plants disclosed in Martin et al., comprise a genomic sequence represented by SEQ ID No. 2.

Example 2

Introduction

White rust is a disease in plants causing major economic losses for crop and flower breeders worldwide. White rust also affects plants in the *Chrysanthemum* genus, and is generally caused by the fungus *Puccinia horiana*. Following infection, pale-green to yellow spots which can be up to 5 mm diameter in size, develop on the upper surface. The centers of these spots become brown and necrotic in time as the plants age. On the lower surface of the leaves, raised, buff or pinkish pustules (telia) develop. The disease is generally carried on infected cuttings and plants, including cut flowers, of glasshouse Chrysanthemums.

Two genomic regions, or genes, genetically linked to molecular markers SEQ ID Nos 1 and 2 affecting resistance have been previously identified, and alleles conferring resistance at each of these loci exist in the varieties an example thereof has been deposited under number NCIMB 42455 and can be obtained through the National Collection of Industrial, Food and Marine Bacteria (NCIMB), Ferguson Building, Craibstone Estate, Bucksburn, Aberdeen AB21 9YA, United Kingdom. While both loci explain substantial amounts of variation in crosses created with the resistant varieties, they fail to explain patterns of resistance in a number of other breeds. For example, some breeds are fully resistant against white rust despite lacking alleles conferring resistance at the loci identified in NCIMB 42455. This suggests that there are, yet unknown, genes which affect resistance in Chrysanthemums. The example presented here has identified one such genomic region, or gene or allele. A plant comprising the present genomic region or gene and SEQ ID No. 3 genetically linked therewith has been deposited under number NCIMB 42762 and can be obtained through the National Collection of Industrial, Food and Marine Bacteria (NCIMB), Ferguson Building, Craibstone Estate, Bucksburn, Aberdeen AB21 9YA, United Kingdom.

Methods

Crossing Scheme and Experimental Setup

To test for associations between SNP markers and resistance profile, an F1 population was created by crossing an individual from the resistant *santini chrysanthemum* selection 08041 with an individual from the susceptible spray *chrysanthemum* selection 02033. Selection 08041 is highly resistant against white rust. 262 F1 individuals (CR15-995004) were then phenotyped for white rust resistance and for each F1 individual 6 clones were assayed. Inoculation with *Puccinia horiana* was done in a blocked design and four tests were performed (at different times) in two containers as described above. Resistance was scored such that large values indicate resistance (a maximum of 9) and low values indicate susceptibility (a minimum of 1). Replicate clones were randomly split between tests and containers. Of these, 80 clones were selected for genotyping. Selection was done to maximize the phenotypic variation present in the genotyped sample, which should increase power to detect SNP-phenotype associations.

Selection 08041 Resistance Locus

Using an Affymetrix SNP array with 50,000 markers for *Chrysanthemum*, the F1 population mentioned above was genotyped, and marker-trait associations were performed within each individual of the F1 population. This yielded 9 single-nucleotide polymorphisms (SNPs) explaining the largest amount of phenotypic variance for white rust resistance in *Chrysanthemum:* 7 SNPs each >50%, and 2 SNPs each over 70%. The latter two SNPS, designated SNP115 and SNP123 were then targeted for a multiplex genotyping-by-sequencing (GBS) approach as they showed the strongest association with white rust resistance. As Chrysanthemums are hexaploid, a method was designed to estimate the number of resistant copies present at a locus within an individual. Individuals of the F1 population between the 08041 and 02033 varieties were then genotyped using this method.

A KASP assay was designed for the SNP115 and SNP123 markers. The KASP method is a more cost-effective method than GBS. A potential disadvantage is that it gives a much cruder measure of the number of resistant copies (KASP ratios can only be 0, 1 or 2) than the dosage ratios estimated from GBS data. The hexaploid nature of Chrysanthemums makes that the number of resistance alleles at a given locus may vary between 0 and 6. Precise knowledge of the number of resistance alleles an individual harbors can be beneficial not only for mapping purposes, but also for selecting individuals during the subsequent breeding stages. Fortunately, the KASP ratios showed to be strongly correlated with dosage ratios obtained by GBS (FIG. 1) meaning that they give a good indication of the number of resistant haplotypes an individual plant harbors. Both parents and all F1 offspring were genotyped using the KASP method.

The KASP primers used for SNP 115 (Assay 4) and SNP 123 (Assay 18) for genotyping are:

```
GxM_WRR_assay4_A (SEQ ID No. 10):
GAAGGTGACCAAGTTCATGCTCAAGTCTTGTACAAYCAAGGAG GxM_WRR_assay4_B (SEQ ID No. 11):
GAAGGTCGGAGTCAACGGATTCAAGTCTTGTACAAYCAAGGAC GxM_WRR_assay4_R (SEQ ID No. 12):
TACACTTAACGAGGATAAATCAC GxM_WRR_assay18_A (SEQ ID No. 13):
GAAGGTGACCAAGTTCATGCTTACAACCAAGGASCAAAACAT GxM_WRR_assay18_B (SEQ ID No. 14):
GAAGGTCGGAGTCAACGGATTTACAACCAAGGASCAAAACAG GxM_WRR_assay18_R (SEQ ID No. 15):
GTCGATTTTCCATACACTTAACG
```

Results

Both among and within the F1 clones derived from offspring of the crosses between the resistant selection 08041 with the susceptible selection 02033 there was heterogeneity in resistance. Based on six replicates, some clones had a mean resistance value of 9 (fully resistant) while other clones had a mean resistance value of 1 (fully susceptible). Some clones showed little heterogeneity (standard deviation of 0 between replicates) while a few others showed larger levels of heterogeneity (standard deviation of 3.7).

The two SNPs which were most strongly associated with white rust resistance in *Chrysanthemum* were 72689_15854_115 (hereafter called SNP 115) and 72689_15854_123 (hereafter referred to as SNP 123) on contig 72689, which maps on Tomato chromosome 1 (96.77 Mb).

The DNA sequence of the haplotype which is shown to confer resistance to white rust is shown below. To facilitate interpretation, SNP115 (G) and SNP 123 (T) are highlighted in bold:

SEQ ID No. 3:
AGCAAAACATGCAGTGATTTATCCTCGTTAAGTGTATGGAAAAT

CGACACCAGGGTGC

Also identified were six haplotypes which were associated with susceptibility in the dataset. SNP 115 and SNP 123 are highlighted in bold and positions where a different nucleotide was found from the resistant haplotype are underlined.

(SEQ ID No. 4)
ACCAAAACAGGCAGTGATTTATCCTCGTTAAGTGTATGGA

AGATCGACACCAGAGTGC (SEQ ID No. 5)
AGCAAAACAGGCAGTGATTTATCCTCGTTAAGTGTATGGA

AGATCGACACCAGAGTGC (SEQ ID No. 6)
ACCAAAACAGGCAGTGATTTATCCTCGTTAAGTGTACGGA

AGATCGACAGCAGGGTGC (SEQ ID No. 7)
ACCAAAACAGGCAGTGATTTATCCTCGTTAAGTGTACGGA

AGATAGACAGCAGGGTGC (SEQ ID No. 8)
AGCAAAACAGGCAGTGATTTATCCTCGTTAAGTGTATGGA

AGATCGACACCAGGGTGG (SEQ ID No. 9)
ACCAAAACAGGCAGTGATTTATCCTCGTTAAGTGTATGGA

AGATCGACACCAGGGTGG

Figure 1:
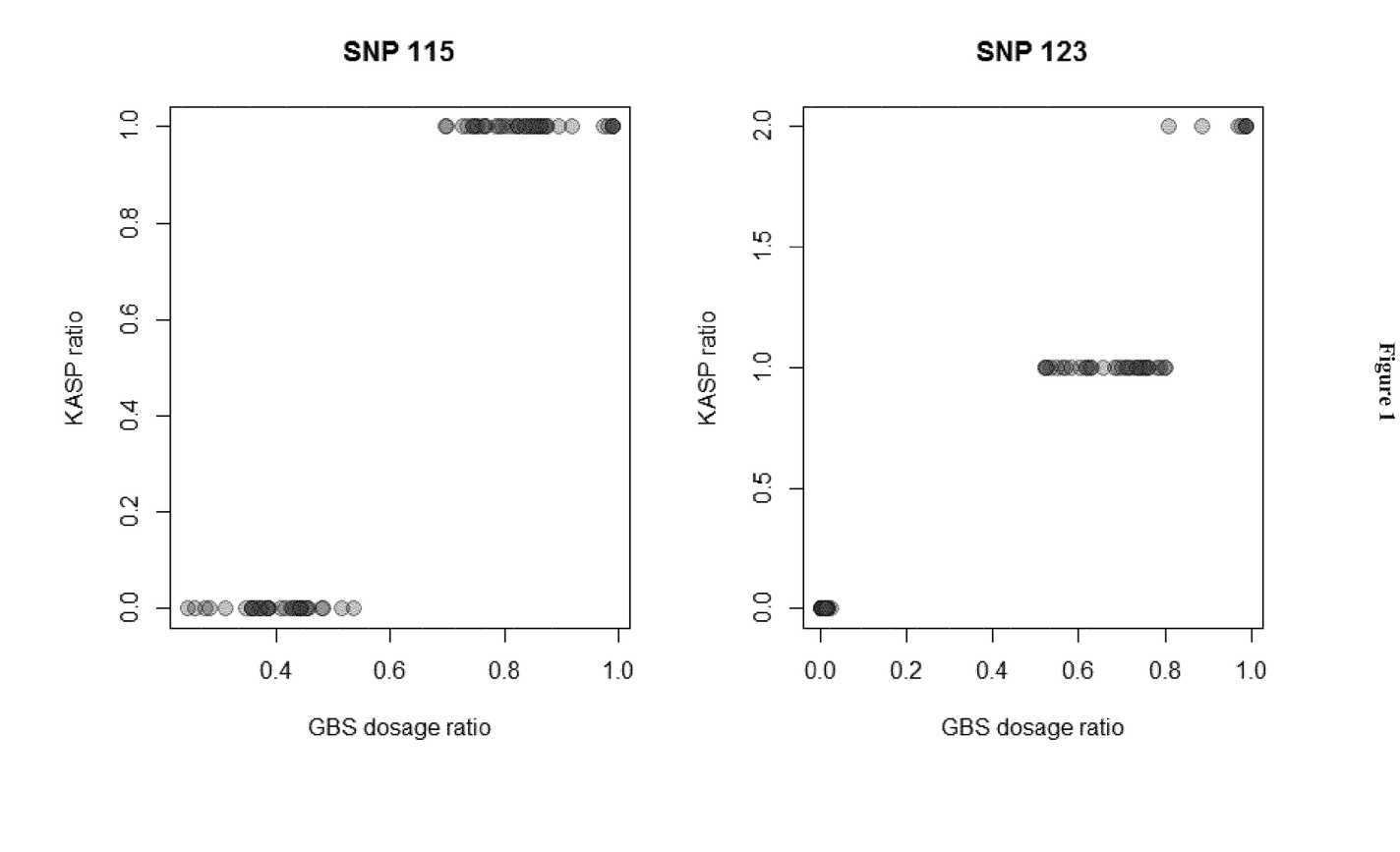
FIG. 1: graphically shows the correlation between the estimated ratio between copies of the resistant allele and the susceptible allele and KASP genotype at two resistance loci (SNP 115 and SNP 123). For both GBS ratio and KASP ratio, a larger value indicates more copies of the resistant allele.
Figure 2:
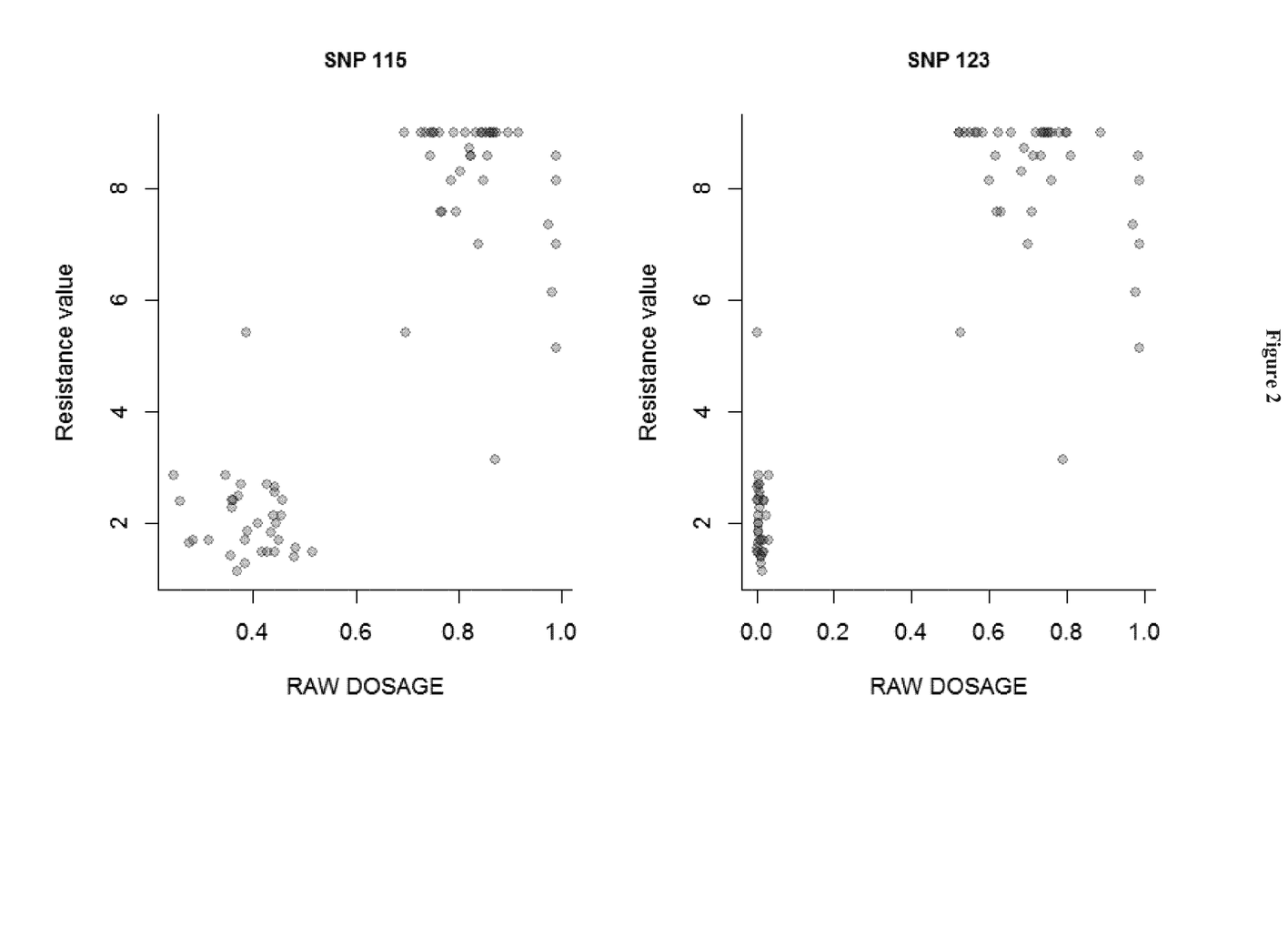
FIG. 2: graphically shows association between genotyping-by-sequencing dosage score and resistance profile at two SNP markers in F1 individuals (selection 08041×selection 02033 cross). At both markers the association was strongly significant as individuals carrying more copies of the resistant allele were generally more resistant.
Figure 3:
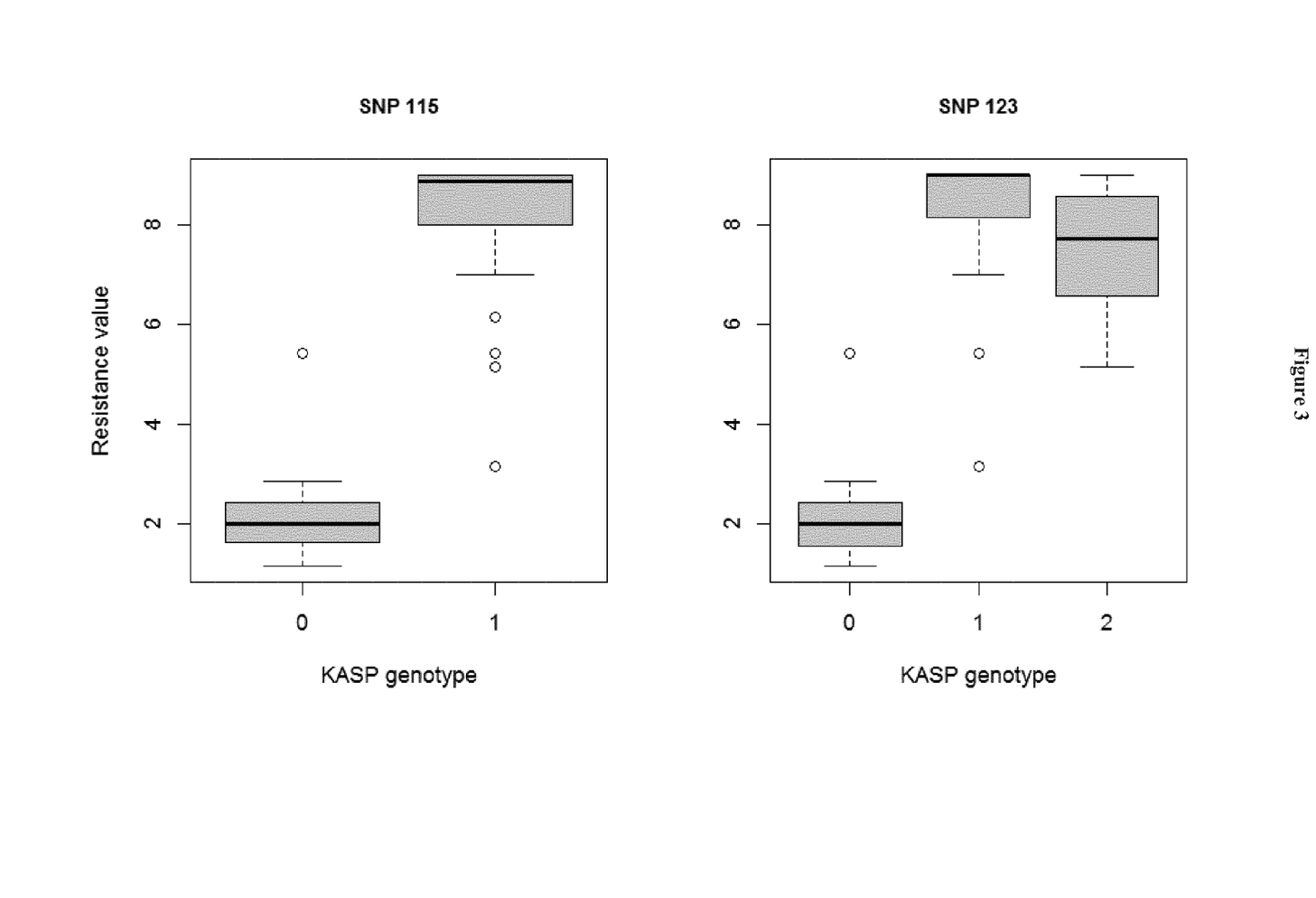
FIG. 3: graphically shows association between KASP genotype score and resistance profile at two SNP markers in F1 individuals (selection 08041×selection 02033 cross). At both markers the association was strongly significant.

There was a clear and strongly significant association (P in all cases $<1*10^{-16}$) between GBS dosage (FIG. 2) and KASP genotype at both loci and the resistance score of the clones (FIG. 3). In the case of SNP 123, where the association between genotypes and resistance shows a pattern that could potentially suggest dominance at this locus. Individuals with a genotype score of 1 are as resistant as individuals with KASP genotype score 2, whereas individuals with genotype class 0 are generally very susceptible (with the exception of one outlier, FIG. 2). However, individuals which are classified as having a KASP genotype of zero can also harbor copies of the resistant haplotype, so more research is needed to clarify if resistance scales additively with the number of resistance copies or whether resistant haplotypes are dominant over susceptible haplotypes. For both SNP markers, there were some genotypes that were more resistant than predicted based on their genotype, while some genotypes were less resistant (FIG. 2). These instances can be explained by a sample swap either in the lab or in the experiment, or by incomplete LD between the resistance allele and the actual (unidentified) gene conferring resistance as it is likely that the identified "resistant" haplotype is close to the gene (as is confirmed by the very significant association between the number of copies of the resistance allele an individual harbors and its resistance profile) but not perfectly linked. As a result, some copies of the resistant haplotype are not perfectly tagging resistant copies of the gene due to recent and/or historical recombination events. Additional alternative explanations are that variants in other genes with small effect are present in either the 08041 or 02033 varieties, or that penetrance of the genetic variants is imperfect.

An interesting observation was that some individuals had a KASP genotype of 2 for SNP 123, whereas the more resistant parent (selection 08041) only had a KASP genotype of 1 (FIG. 3). This was surprising as this suggests that some F1 offspring have more copies of the resistant haplotypes at this region than selection 08041, which is contrary to expectation. Hence we have investigated the segregation of GBS dosage ratios in the F1 in more details.

Figure 4:
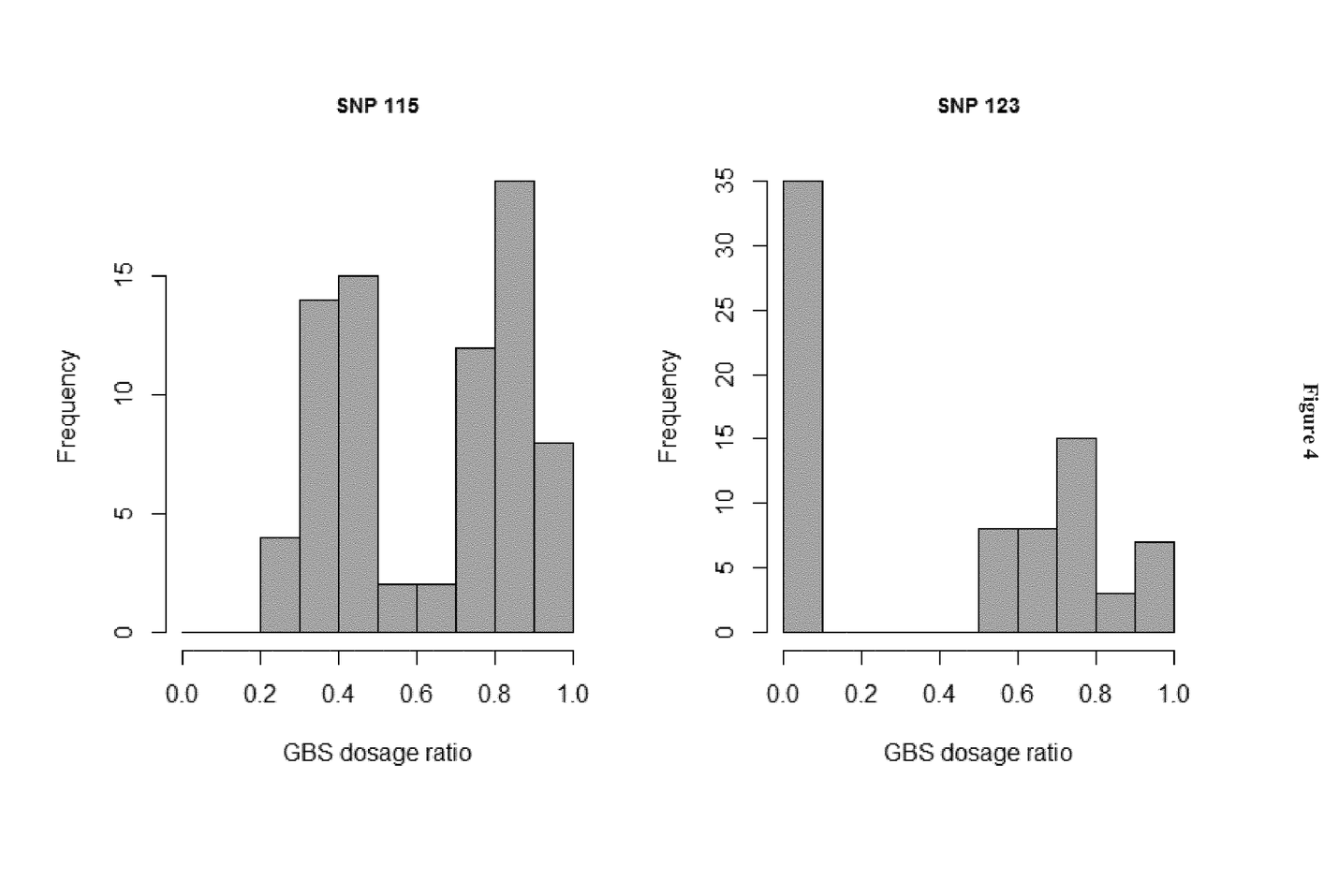
FIG. 4: shows histograms showing the distributions of multiplex GBS dosage ratios in the F1 offspring. A larger GBS ratio indicates that that individual carries more "resistant" copies of the haplotype described.

We found the distribution of dosage ratios at SNP 123 highly unusual (FIG. 4). And as the dosage ratios of the parents were unknown we used simulations to test if we could replicate these distributions. We simulated crosses between parents each having one of 7 possible genotypes at the locus of interest (AAAAAA, BAAAAA, BBAAAA, etc.). For each of 49 pairwise crosses we then drew gametes at random assuming polysomic inheritance resulting in a hexaploid genotype in the offspring. This process was repeated at random for a total of 50 times.

If we look at the simulated distributions, we observe that for SNP 115 the empirical distribution of dosage ratios most closely resembles that of a scenario where the most resistant parent has five copies of the resistance alleles and the susceptible parent had two copies of the resistant haplotype. For SNP 123 the observed distribution of dosage ratios does not match any of the simulated combinations of parent pairs. Whether this discrepancy has a biological or technical explanation deserves to be investigated in the future, starting with genotyping the parental lines.

CONCLUSION

Precise knowledge of the genes and variants thereof which influence white rust (*Puccinia horiana*.) resistance is pivotal for the breeding of more resistant *Chrysanthemum* varieties. Two major effect loci have been previously identified (SEQ ID Nos 1 and 2).

It was hypothesized that there must be other genes which can confer resistance to white rust in Chrysanthemums. The results presented here unequivocally show that variants at two closely linked SNP markers can strongly predict resistance, suggesting that these SNPs and the haplotype they are found one, are in tight linkage with causal genes.

The invention claimed is:

1. A white rust resistant plant belonging to the genus *Chrysanthemum*, comprising in its genome at least one genomic region, gene, or allele providing white rust resistance, said at least one genomic region, gene, or allele providing white rust resistance being genetically linked to a nucleic acid having the sequence of SEQ ID No. 3, seed of said plant having been deposited with NCIMB under Accession No. NCIMB 42762.

2. The plant according to claim 1, wherein said plant further comprises in its genome a further genomic region, gene, or allele providing white rust resistance, said further white rust resistance providing genomic region, gene, or allele being genetically linked to a nucleic acid having the sequence of SEQ ID No. 2.

3. The plant according to claim 1, wherein said plant further comprises in its genome a further genomic region, gene, or allele providing white rust resistance, said further white rust resistance providing genomic region, gene, or allele being genetically linked to a nucleic acid having the sequence of SEQ ID No. 1.

4. The plant according to claim 1, wherein said plant further comprises in its genome a further genomic region, gene, or allele providing white rust resistance, said further white rust resistance providing genomic region, gene, or allele being genetically linked to a nucleic acid having the sequence of SEQ ID No. 2, and wherein said plant further comprises in its genome a second further genomic region, gene, or allele providing white rust resistance, said second further white rust resistance providing genomic region, gene, or allele being genetically linked to a nucleic acid having the sequence of SEQ ID No. 1.

5. The plant according to claim 1, wherein said plant comprises five copies or less of a nucleic acid having a sequence selected from the group consisting of SEQ ID No. 4, SEQ ID No. 5, SEQ ID No. 6, SEQ ID No. 7, SEQ ID No. 8, and SEQ ID No. 9.

6. The plant according to claim 1, wherein said plant is a cut *Chrysanthemum* or said plant is a pot *Chrysanthemum*.

7. The plant according to claim 1, wherein a causative pathogen of said white rust is *Puccinia horiana*.

8. The plant according to claim 1, wherein said plant comprises in its genome at least three genomic regions, genes, or alleles providing white rust resistance, the first genomic region, gene, or allele providing white rust resistance being genetically linked to the genomic nucleic acid having the sequence of SEQ ID No. 3, the second genomic region, gene, or allele providing white rust resistance being genetically linked to a genomic nucleic acid having the sequence of SEQ ID No. 2, and the third genomic region, gene, or allele providing white rust resistance being genetically linked to a genomic nucleic acid having the sequence of SEQ ID No. 1.

9. The plant according to claim 1, wherein said plant is a *Chrysanthemum* x *morifolium* plant, and wherein said plant is resistant to the white rust pathogen *Puccinia horiana*.

10. A seed, plant part or plant cell of the *Chrysanthemum* plant according to claim 1, wherein said seed, plant part or plant cell comprises said at least one genomic region, gene, or allele providing white rust resistance being genetically linked to a nucleic acid having the sequence of SEQ ID No. 3.

11. A progeny of the *Chrysanthemum* plant according to claim 1, wherein said progeny comprises said at least one genomic region, gene, or allele providing white rust resistance being genetically linked to a nucleic acid having the sequence of SEQ ID No. 3.

12. The progeny of the *Chrysanthemum* plant according to claim 11, wherein said progeny further comprise in its genome a further genomic region, gene, or allele providing white rust resistance, said further white rust resistance providing genomic region, gene, or allele being genetically linked to a nucleic acid having the sequence of SEQ ID No. 2 or SEQ ID No. 1.

13. A *Chrysanthemum* plant grown from seed deposited with NCIMB under Accession No. NCIMB 42762, wherein the *Chrysanthemum* plant is resistant to white rust and comprises in its genome SEQ ID NO: 3.

14. A seed, plant part, or plant cell of the *Chrysanthemum* plant of claim 13, wherein the seed, plant part, or plant cell is resistant to white rust and comprises in its genome SEQ ID NO: 3.

15. A method for producing a progeny *Chrysanthemum* plant that is resistant to white rust, the method comprising crossing a first *Chrysanthemum* plant that is resistant to white rust, said first plant grown from a seed deposited with NCIMB under Accession No. NCIMB 42762 with a second *Chrysanthemum* plant to generate offspring; and selecting one or more progeny *Chrysanthemum* plants that are resistant to white rust and comprise in their genome SEQ ID NO: 3.

16. The method of claim 15, wherein said progeny further comprises in its genome a further genomic region, gene, or allele providing white rust resistance, said further white rust resistance providing genomic region, gene, or allele being genetically linked to a nucleic acid having the sequence of SEQ ID No. 2 or SEQ ID No. 1.

17. The method of claim 15, wherein said progeny comprise five copies or less of a nucleic acid having a sequence selected from the group consisting of SEQ ID No. 4, SEQ ID No. 5, SEQ ID No. 6, SEQ ID No. 7, SEQ ID No. 8, and SEQ ID No. 9.

18. The method of claim 15, wherein a causative pathogen of said white rust is *Puccinia horiana*.

19. A seed, plant part, or plant cell of a progeny plant produced by the method of claim 15, wherein said seed, plant part or plant cell comprises at least one genomic region, gene, or allele providing white rust resistance being genetically linked to a nucleic acid having the sequence of SEQ ID No. 3.

20. The method according to claim 15, wherein said second *Chrysanthemum* plant is selected from the group consisting of *Chrysanthemum* x *morifolium*; *Chrysanthemum* x *grandiflorum*; *Chrysanthemum* x *rubellum*; *Chrysanthemum abolinii*; *Chrysanthemum achillaea* L.; *Chrysanthemum alabasicum*; *Chrysanthemum brachyanthum*;

*Chrysanthemum carinatum*; *Chrysanthemum chalchingolicum*; *Chrysanthemum cinerariifolium*; *Chrysanthemum coccineum*; *Chrysanthemum coreanum*; *Chrysanthemum coronarium*; *Chrysanthemum decaisneanum*; *Chrysanthemum delavayanum*; *Chrysanthemum dichrum*; *Chrysanthemum fastigiatum*; *Chrysanthemum frutescens*; *Chrysanthemum gracile*; *Chrysanthemum grubovii*; *Chrysanthemum horaimontanum*; *Chrysanthemum hypoleucum*; *Chrysanthemum indicum* L.; *Chrysanthemum junnanicum*; *Chrysanthemum kinokuniense*; *Chrysanthemum kokanicum*; *Chrysanthemum konoanum*; *Chrysanthemum majus*; *Chrysanthemum marginatum*; *Chrysanthemum mawei*; *Chrysanthemum maximum* L.; *Chrysanthemum miyatojimense*; *Chrysanthemum morifolium*; *Chrysanthemum multifidum*; *Chrysanthemum nitidum*; *Chrysanthemum parvifolium*; *Chrysanthemum przewalskii*; *Chrysanthemum purpureiflorum*; *Chrysanthemum ramosum*; *Chrysanthemum rhombifolium*; *Chrysanthemum roborowskii*; *Chrysanthemum segetum*; *Chrysanthemum shihchuanum*; *Chrysanthemum shimotomaii*; *Chrysanthemum trilobatum*; *Chrysanthemum tripinnatisectum*; *Chrysanthemum vestitum*; *Chrysanthemum vulgare* (L.); *Chrysanthemum yoshinyanthemum*; and *Chrysanthemum zawadskii*.

\* \* \* \* \*

SEQUENCE LISTING

<160> NUMBER OF SEQ ID NOS: 15

<210> SEQ ID NO 1
<211> LENGTH: 192
<212> TYPE: DNA
<213> ORGANISM: Chrysanthemum genus

<400> SEQUENCE: 1

```
ttaactcaaa aatatgacta caaatcaatt ttcaggactt tttttcgata cttccctctt    60
tggtaccggt accgtattag tggtaccgat ttttttgggg ctcaattcat ggtacaggca   120
ccgtaccgtg tattgggagt cggtaccgtt tcgatacggt accggtacgg ttccgattcg   180
ataccggaat tc                                                      192
```

<210> SEQ ID NO 2
<211> LENGTH: 180
<212> TYPE: DNA
<213> ORGANISM: Chrysanthemum genus

<400> SEQUENCE: 2

```
gaattcctat acgaaggttt tgtagatgtg tctccgagcg agtttgatcc taactcacga    60
ctagtaattt atgtccataa aaccgataac ttgaacattc cctcttgttc ttgtagatgg   120
ggatgacttc actgagtctc cattcttctg gcatcttatc actggaaaaa atcttgttaa   180
```

<210> SEQ ID NO 3
<211> LENGTH: 58
<212> TYPE: DNA
<213> ORGANISM: Chrysanthemum genus

<400> SEQUENCE: 3

```
agcaaaacat gcagtgattt atcctcgtta agtgtatgga aaatcgacac cagggtgc     58
```

<210> SEQ ID NO 4
<211> LENGTH: 58
<212> TYPE: DNA
<213> ORGANISM: Chrysanthemum genus

<400> SEQUENCE: 4

```
accaaaacag gcagtgattt atcctcgtta agtgtatgga agatcgacac cagagtgc     58
```

<210> SEQ ID NO 5
<211> LENGTH: 58
<212> TYPE: DNA
<213> ORGANISM: Chrysanthemum genus

<400> SEQUENCE: 5

```
agcaaaacag gcagtgattt atcctcgtta agtgtatgga agatcgacac cagagtgc     58
```

<210> SEQ ID NO 6
<211> LENGTH: 58
<212> TYPE: DNA
<213> ORGANISM: Chrysanthemum genus

<400> SEQUENCE: 6

```
accaaaacag gcagtgattt atcctcgtta agtgtacgga agatcgacag cagggtgc     58
```

<210> SEQ ID NO 7
<211> LENGTH: 58
<212> TYPE: DNA
<213> ORGANISM: Chrysanthemum genus

<400> SEQUENCE: 7

```
accaaaacag gcagtgattt atcctcgtta agtgtacgga agatagacag cagggtgc     58
```

<210> SEQ ID NO 8
<211> LENGTH: 58
<212> TYPE: DNA
<213> ORGANISM: Chrysanthemum genus

<400> SEQUENCE: 8

```
agcaaaacag gcagtgattt atcctcgtta agtgtatgga agatcgacac cagggtgg        58

<210> SEQ ID NO 9
<211> LENGTH: 58
<212> TYPE: DNA
<213> ORGANISM: Chrysanthemum genus

<400> SEQUENCE: 9
accaaaacag gcagtgattt atcctcgtta agtgtatgga agatcgacac cagggtgg        58

<210> SEQ ID NO 10
<211> LENGTH: 43
<212> TYPE: DNA
<213> ORGANISM: Artificial Sequence
<220> FEATURE:
<223> OTHER INFORMATION: KASP primer for SNP 115

<400> SEQUENCE: 10
gaaggtgacc aagttcatgc tcaagtcttg tacaaycaag gag                        43

<210> SEQ ID NO 11
<211> LENGTH: 43
<212> TYPE: DNA
<213> ORGANISM: Artificial Sequence
<220> FEATURE:
<223> OTHER INFORMATION: KASP primer for SNP 115

<400> SEQUENCE: 11
gaaggtcgga gtcaacggat tcaagtcttg tacaaycaag gac                        43

<210> SEQ ID NO 12
<211> LENGTH: 23
<212> TYPE: DNA
<213> ORGANISM: Artificial Sequence
<220> FEATURE:
<223> OTHER INFORMATION: KASP primer for SNP 115

<400> SEQUENCE: 12
tacacttaac gaggataaat cac                                              23

<210> SEQ ID NO 13
<211> LENGTH: 42
<212> TYPE: DNA
<213> ORGANISM: Artificial Sequence
<220> FEATURE:
<223> OTHER INFORMATION: KASP primer for SNP 123

<400> SEQUENCE: 13
gaaggtgacc aagttcatgc ttacaaccaa ggascaaaac at                         42

<210> SEQ ID NO 14
<211> LENGTH: 42
<212> TYPE: DNA
<213> ORGANISM: Artificial Sequence
<220> FEATURE:
<223> OTHER INFORMATION: KASP primer for SNP 123

<400> SEQUENCE: 14
gaaggtcgga gtcaacggat ttacaaccaa ggascaaaac ag                         42

<210> SEQ ID NO 15
<211> LENGTH: 23
<212> TYPE: DNA
<213> ORGANISM: Artificial Sequence
<220> FEATURE:
```

-continued

```
<223> OTHER INFORMATION: KASP primer for SNP 123

<400> SEQUENCE: 15
gtcgattttc catacactta acg                                              23
```

UNITED STATES PATENT AND TRADEMARK OFFICE
CERTIFICATE OF CORRECTION

PATENT NO. : 11,122,755 B2
APPLICATION NO. : 16/335388
DATED : September 21, 2021
INVENTOR(S) : Paulus Cornelis Maris et al.

Page 1 of 1

It is certified that error appears in the above-identified patent and that said Letters Patent is hereby corrected as shown below:

On the Title Page

Item (73), Assignee, Line 1, after "B.V." insert -- , (NL) --

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*